United States Patent
Becker et al.

(10) Patent No.: US 8,380,809 B2
(45) Date of Patent: Feb. 19, 2013

(54) PROVIDING A NUMBER OF WEB SERVICES FOR IMAGING OPTIONAL MEDICAL APPLICATIONS

(75) Inventors: Detlef Becker, Möhrendorf (DE); Lutz Dominick, Eggolsheim (DE); Karlheinz Dorn, Kalchreuth (DE); Andrew John Hewett, Erlangen (DE); Artur Pusztai, Erlangen (DE); Subrata Sinha, Erlangen (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 948 days.

(21) Appl. No.: 12/379,979

(22) Filed: Mar. 5, 2009

(65) Prior Publication Data

US 2010/0229153 A1    Sep. 9, 2010

(51) Int. Cl.
*G06F 15/16*    (2006.01)
(52) U.S. Cl. ......................................... 709/217; 709/203
(58) Field of Classification Search .................. 709/203, 709/217–218; 717/107
See application file for complete search history.

(56) References Cited

U.S. PATENT DOCUMENTS

| | | | |
|---|---|---|---|
| 2005/0251020 A1* | 11/2005 | Kondo et al. | 600/407 |
| 2008/0082966 A1* | 4/2008 | Dorn et al. | 717/120 |
| 2008/0228781 A1* | 9/2008 | Chen et al. | 707/10 |
| 2009/0089109 A1* | 4/2009 | Rabetge et al. | 705/7 |
| 2009/0157695 A1* | 6/2009 | Roberts | 707/10 |
| 2009/0165114 A1* | 6/2009 | Baum et al. | 726/12 |
| 2009/0227877 A1* | 9/2009 | Tran | 600/483 |
| 2010/0094649 A1* | 4/2010 | White | 705/2 |
| 2010/0186017 A1* | 7/2010 | Eeratta et al. | 718/104 |

FOREIGN PATENT DOCUMENTS

| | | |
|---|---|---|
| EP | 1 906 304 | 4/2008 |
| EP | 1906304 A2 | 4/2008 |

\* cited by examiner

*Primary Examiner* — Jason Recek
(74) *Attorney, Agent, or Firm* — Harness, Dickey & Pierce, PLC

(57) ABSTRACT

A system and a computer-implemented method are disclosed, as well as a computer readable medium, for providing a number of web services for at least one medical viewing application, so as to provide the application with application-exceeding basic functionalities with regard to a transfer management service, a data management service, a workflow management service, a report management service, a protocol management service, an operating management service and an enterprise application integration management service. A web service of at least one embodiment, in that case, includes at least one remote service component, at least one business object and at least one service component.

30 Claims, 2 Drawing Sheets

PROVIDING A NUMBER OF WEB SERVICES FOR IMAGING OPTIONAL MEDICAL APPLICATIONS

FIELD

At least one embodiment of the present invention is in the field of data processing and medical technology and generally relates to providing a number of web services for a medical application.

BACKGROUND

The development of software applications in the field of image-processing medical technology differs from that in other fields because it must take into consideration special protocols and additional specific characteristics of the medical domain. The software development in this field consequently requires specifically adapted software solutions, for example solutions adapted to the high volume of image data to be transferred, to increased electronic networking, or to the increasing complexity of the clinical tasks to be managed.

In the past, software applications in the medical field were also produced monolithically, meaning that if changes were required it was always necessary to modify the complete application unit. This process was always tied to extremely high expenditure and was also susceptible to errors. For that reason, a change was made to developing medical software applications with the aid of high-performance, generic, so-called frameworks. The generic frameworks are used to increase the productivity of the application development. Examples of such frameworks are .NET, J2EE and OpenGL. The disadvantage of these generic frameworks is seen in the fact that so far they have not been tailored to the medical domain, so that the application development for the most part must still be realized manually, despite the use of the generic framework.

One example of a medical framework is described in the cited document EP 1 906 304, to which we refer with respect to content in the present patent application. The disadvantage of using frameworks that are directed specifically to the medical domain, however, is that the respective application is so-to-speak fixedly linked to the respective framework. As a result, a replacement of specific framework components or the replacement of a framework with a better framework, for example that of another manufacturer, is only possible with limitations or not at all.

The structure of medical applications generally comprises several layers with respectively different components. This problem is made worse when considering a free component selection, flexibility and improved ability to replace components because the involved application components generally have very complex dependencies, so that a change made for one component usually requires a cascade of changes to other components.

SUMMARY

At least one embodiment of the present invention improves the development of applications used in the field of medical technology, especially for the imaging medical technology. In particular, one goal of at least one embodiment is to make the application development more flexible and to ensure that the components used for an application can be replaced easier. In addition, the goal is to simplify the software development and to show a path for respectively selecting the most cost-effective technical and optimal implementation. It should furthermore be possible to make changes to individual functionalities of the application, without having to adapt and modify the application.

Any features, advantages or alternative embodiments mentioned in the process must also be transferred to the other claimed objects and vice versa. In other words, the additional claims (for example directed toward a method or a product), can also be modified with the features that are described or claimed in connection with the system. The respective functional features of the method are embodied with corresponding modules, in particular hardware modules, for the system and/or the product.

At least one embodiment of the invention in particular relates to a system for providing a number of web services for at least one medical application in the field of image-processing medical technology, so as to provide application-exceeding basic functionalities for the medical application, wherein respectively one web service implements at least one basic functionality and wherein all web services are respectively configured based on the same diagram and comprise at least the following components:

- at least one remote-service component, which allows respectively one application to access at least one web service;
- at least one business object in which the respective basic functionality is implemented and which can be used by a remote service component; and
- at least one service component, which provides selected, different basic functionalities and can be used by a remote service component.

The concepts used within the framework of at least one embodiment of this invention are explained in further detail in the following.

The so-called web services are software applications, which make available a specific basic functionality to a client or an application. The web services can be accessed via a network, in particular the Internet. As a rule, they are based on a service-oriented architecture (SOA) and convert distributed and/or object-oriented standards. The web services provided within the framework of this patent application relate to clinical and/or medical applications in the broader sense and can also be administration-specific and organization-specific. In the same way, the applications can relate, for example, to control methods for a configuration of medical devices.

Within the framework of at least one embodiment of this invention, the medical application is in the field of the image-processing technology and, in particular, relates to viewing applications. These are preferably based on a data transfer according to the DICOM standard (DICOM=digital imaging and communications in medicine), which—if applicable together with patient data or report data—is used to draw up, modify, transfer to and/or store in a different node of a clinical network, e.g. medical modalities, computers, servers, databases or other data-processing systems, a clinical finding or a report.

The basic functionality is an application-exceeding functionality that is relevant for all medical applications. One important aspect of at least one embodiment of the present invention therefore is that it defines a specific set and/or a set of basic functionalities, meaning a set of seven basic functionalities. These functionalities comprise: the transfer management, data management, workflow management, report management, protocol management, operating management and the enterprise application integration management (EAI management). One essential advantage of using this fixedly-defined set of basic functionalities therefore is that all functionalities of medical viewing applications can be covered with these basic functionalities. A detailed description of the aforementioned basic functionalities will be provided later on.

A web service has a modular design and comprises at least three components: at least one remote service component, at least one business object and at least one service component.

The remote service component is a component of the web service and functions to allow access to the respective web service. A remote service component is a component with a web-service interface. A remote service component can also comprise additional and special sub components, such as the provider objects and (local) service components. As a rule, a web service comprises several remote service components. Depending on the degree of complexity and the application case, a web service can also comprise only one remote service component. The combined number of all interfaces for all remote service components of the web service then forms the API interface (application programming interface), which is the programming interface for the respective web service. The web services use these APIs for utilizing the web service functionality.

In a business object, the respective basic functionality is implemented. A remote service component can offer several such business objects. The business objects can also be exchanged in order to change a specific functionality of the respective web service, which is possible without having to change the respective application.

A service component combines selected and different basic functionalities, which can be used by a remote service component. A remove service component can use several such service components. The service components are generated in such a way that it is not always necessary to implement the complete basic functionality of a web service within remote service components, but to allow the use of only a selected number of the available basic functionalities. The advantage is that the service components can also be used by several remote service components. Service components—in the same way as remote service components—can comprise business objects which, when replacing them with other business objects, can be used to adapt the respective web service functionality.

According to one example embodiment of the present invention, the respective application directly accesses the web service. Alternatively or cumulatively, the application can also access the web service indirectly via a framework, in which case the web services are loosely coupled to the frameworks. The web services can thus advantageously be exchanged easily (because from a logical point of view they are not hard wired) and can be replaced by other services or can also be modified in different ways, for example through web services of other producers.

According to a different advantageous embodiment, the web service can be executed in a development environment for the application to be generated and/or a running-time environment for the application. In other words, the system according to at least one embodiment of the invention can be used as tool within the framework of the software development and as tool for supporting the application.

The web services made available to the application can preferably be addressed in a programming-language and platform-independent description language, wherein the access preferably occurs via WSDL (Web Service Description Language) as XML-based meta-language. However, alternatives or expansions, e.g. WSDL-S or OGSA (open grid service architecture) can also be used for this, thus making it possible to achieve further flexibility.

The flexibility of the system according to at least one embodiment of the invention is also increased in that the system is based on a programming language, platform and protocol independent architecture. In other words, the system can be used with optional programming languages, platforms and protocols. One essential advantage is the fact that the system can also be used with system already in use, thus resulting in a clearly positive cost balance.

In the following, the set of selected web services is to be explained further and, in particular, the seven defined basic functionalities are to be described in further detail.

The transfer management provides the basic functionality to the DICOM transfer of medical image data sets. The transfer management is used to request information on available storage media (e.g. media devices) on a machine (e.g. a computer or a computer-supported system or a modality). In addition, characteristics of the available storage media should be made available, such as the dimensions of the storage medium, the available capacity and the like and the data transfer realized to the available and suitable media. The transfer management functionality comprises two remote service components: a media access component that supplies information on available storage media on a computer along with their characteristics, as well as a remote service component, namely a network listener component. The network listener component monitors a specific port of a machine via a socket. When data arrive at the socket, the network listener component activates the respective processing steps, for example by initiating a query of specific DICOM nodes in the network. A storage commit SCU and a perform procedure step (PPS) can also be initiated.

The second web service in the set of web services relates to the data management. The data management service is used to obtain access to data systems on remote computers. In addition, it offers access to indexed DICOM data. The data management comprises two remove service components. A data management component allows access to an index repository of DICOM data stored in a database. A file access component allows access to the file system of a remote computer.

The third service in the set of available web services relates to the workflow management, which is responsible for the control of different medical applications for clinical sequences and/or procedures. The workflow management comprises two remove service components. A workflow component delivers role-specific work lists and permits a mapping of clinical procedures for the applications to be run. In addition, it automatically starts the applications for a clinical procedure and furthermore establishes a link between the incoming data and the respective application. The second component is an information component, which administers demographic patient data, makes available search functions for these data, and is embodied for administering and distributing performed-procedure steps information. The information component implements the interface information management.

The fourth web service from the set of web services relates to the report management. The report management allows combining individual applications, individual application-specific partial reports (also called evidence documents) into a complete and uniform report. The report management service includes only one remote service component, which is a common reporting data component. The common data reporting data component is responsible for transferring the individual, separate evidence documents into a joint data model and consolidate these into a uniform report.

In the following, we want to introduce the protocol management as the fifth web service within the framework of the set of web services. The protocol management service is intended to administer and distribute the protocols for transferring medical imaging data. In particular, the protocols are administered with respect to the medical modalities. The protocol management service comprises a protocol management component and a protocol distribution component, which can both access in turn a database management system. The protocol management component is a component that provides access to a database of the acquisition protocols, which can be administered in this database. The protocol distribution component is a component responsible for distributing protocols. For this, the protocol distribution component can also communicate with external devices, e.g. medical modalities.

The sixth web service relates to the operating management and comprises a number of all-encompassing, supporting services for medical applications. The operating management service provides functionalities for monitoring resources on the computer, on which the framework and/or the respective web service is installed. The operating management comprises seven components, preferably a GSM component, a CoLicenseManager component, a message-store component, a central audit component, a central utilization component, a central log component and a depot component. The GSM component (GSM—global session management) makes possible the global user session administration. The advantage is that a user needs to log on to an application only once to be able to use all other applications within the network. Without the GSM component, the user would have to log on separately for each application.

The CoLicenseManager component administers licenses for software applications. The message-store component administers messages system-wide with regard to errors, general information, debugging information, audit information and the like. The central-audit component functions as central memory for audit messages. The central-utilization component functions as central memory for application messages. The central-log component functions as central memory for the log-on information. The depot-component functions as a memory for storing all software applications, which can be installed within the network.

The final web service to be described is the enterprise-application-integration subsystem. This subsystem is designed to provide the basic functionality for linking to other medical systems via standard protocols and is, so-to-speak, a protocol converter, which operates in particular based on the HL7 standard, wherein other standards can also be used. The EAI functionality allows the interaction and/or the data exchange with any other optional systems via the exchange of messages. This type of web service in particular allows sending and receiving messages, especially messages from the OpenLink protocol for communicating with other external medical or non-medical systems. The OpenLink remote service component implemented the OpenLink protocol and offers two Interfaces linking to the outside: ReceivedMessage and ISendMessage.

One advantage of the fixedly defined set of web services and their basic functionalities is that the expenditure for generating applications can be noticeably reduced. The web services provided implement frequently used functionalities in the medical field, so that the application development can concentrate exclusively on the implementing of the actual application functionality, without unnecessarily using resources for the implementing of basic functionalities (e.g. data transfer, general communication and the like).

In addition, the use of the web services can noticeably reduce the time for the application development, which on the whole implies a reduced time to market and lower costs for the total system.

One essential advantage must also be seen in the uniform structuring of the components used, thus making it easy and simple to replace the modular system and making it easier to use individual web services or components thereof in different applications. In addition, the components can also be replaced with those of other producers, thereby further increasing the flexibility.

We again want to mention here that the aforementioned number of web services must only be understood to be an example. The number of the web services provided can be expanded at any time and easily by using additional web services. Individual web services with less complex embodiments can furthermore be deleted from this list, so that only an underlying number of basic functionalities are provided.

At least one embodiment is furthermore directed to a method and a computer program as disclosed in the enclosed main claims. The embodiments, features and advantages mentioned in connection with the system can also be transferred to the computer program product.

The above-described embodiments of the inventive method can also take the form of a computer program product, wherein the computer is triggered to realize the above-described method according to the invention if the program is run on the computer and/or a processor for the computer.

An alternative solution provides for a storage medium for storing the above-described computer-implemented method and which can be read by a computer.

In addition, it is possible to design the individual components of the above-described method as a marketable unit and to embody the remaining components as a different marketable unit, so-to-speak in the form of a distributed system.

BRIEF DESCRIPTION OF THE DRAWINGS

The following detailed description of the Figures, which is not intended to be restrictive, discusses the features and advantages of the example embodiments with the aid of the drawing, which shows in.

Corresponding configurations and/or components are provided with the same reference numbers in the Figures.

DETAILED DESCRIPTION OF THE EXAMPLE EMBODIMENTS

Figure 1A:
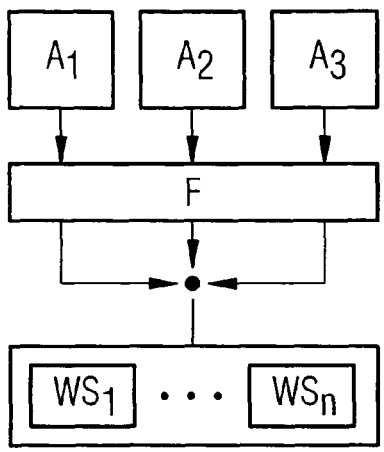
FIG. 1 An overview-type representation of a basic configuration for web services, wherein a framework is used in FIG. 1a and no such framework is used in FIG. 1b.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The structural context of the system according to an embodiment of the invention is explained further in the following with the aid of the FIGS. 1a and 1b.

Three applications A1, A2 and A3 are shown in the upper portion of FIG. 1a, which are representative for a plurality of medical applications. The applications A advantageously refer to medical visualization applications. To make the development of medical applications easier, the use of frameworks F is known from the prior art. A known framework F is the .NET framework by the company Microsoft Corporation, which is based on a configuration with n layers and offers the option of using different programming languages such as Visual Basic, .NET, C++, JScript, Javascript.NET and the like. The .NET framework comprises as language converter, which makes it possible to convert the respectively used programming language into a common intermediate language (CIL). Other frameworks F are J2EE and Open GL. The .NET and the J2EE framework respectively comprise a plurality of generic subsystems, which can be used for the application development to implement the respectively desired functionality of the application A.

For example, the framework F as a rule contains subsystems for the communication functionality, so that all functionalities can be covered with regard to an interaction of the respective application A with other components. It has turned out to be a problem in this connection that the medical domain in many respects requires a special treatment, for example it involves as a rule extremely high data volumes to be able to transfer DICOM images. Specific functionalities for image-processing medical applications cannot be derived from the F framework. Starting with this, the cited reference EP 1 906 304, the entire contents of which is hereby incorporated herein by reference, discloses an approach to providing domain-specific frameworks with the corresponding functionality for the medical field. For this, the applications A access the framework F, wherein the framework F in turn can access different web services WS via a uniform Interface. The web services WS are shown in the lower portion of FIG. 1 with the respective references WS1, . . . WSn.

If we were to use such a framework F, the application A could also directly access the available web services WS. This scenario is shown in FIG. 1b, wherein the respective web services WS are loosely linked to the framework F, thereby resulting in the advantage that the respective web services WS can be replaced easily with the web services WS from other producers. The application development can thus be clearly improved on the whole because it can be provided faster and cheaper. In the same way, the web services WS, which are used by the respective applications A without a framework F—as shown in FIG. 1b—are also linked loosely to the respective applications A and can thus be replaced easily.

Figure 1B:
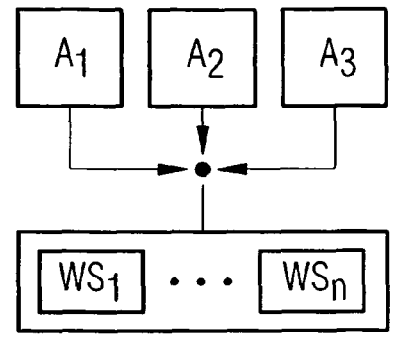

As indicated in FIGS. 1a and 1b, the web services WS in the form of WS1, WS2, ... WSn are accessed via a uniform interface, which also noticeably reduces the programming expenditure.

In connection with FIG. 2, the basic configuration of a respective web service WS is described in the following in further detail.

As previously explained in connection with FIG. 1, an application A can access a web service WS directly or indirectly. As shown in FIG. 2 with the dashed square, the web service WS comprises several components, that is to say one or generally several remote service components RSC. As a rule, these comprise several business objects BO and one or generally several service components SC.

In addition, a remote service component RSC can also comprise several sub components, for example provider objects and (local) service components SC. All interfaces of all remote service components RSC taken together, meaning so-to-speak the combined number of all interfaces of all remote service components RSC, of the web services WS jointly form the programming interface (application programming interface—API) of the respective web service WS. This is shown in FIG. 2 by the connecting line pointing to the left outside, which starts with the remote service component RSC and which is shown in FIG. 2 as a dot representing the interface to the application A. The applications A utilize the APIs for accessing the functionality of the respective web services WS.

A remote service component RSC can offer business objects BO. These can be replaced to change a specific functionality of the web services WS in that different web services can be replaced easily with the preceding web services WS.

A remote service component RSC can use several service components SC. These service components are generated to avoid having to always implement the complete functionality of a web service WS within a remote service component RSC. For example, if only a selection [selected component?] from this functionality is sufficient, then a service component SC can be defined which then provides this selection. The service components SC can be used by several different remote service components RSC. In addition, the service components SC can comprise business objects BO, wherein these business objects BO in turn can be replaced by other business objects BO' to adapt and/or change the functionality on the whole.

Figure 2:
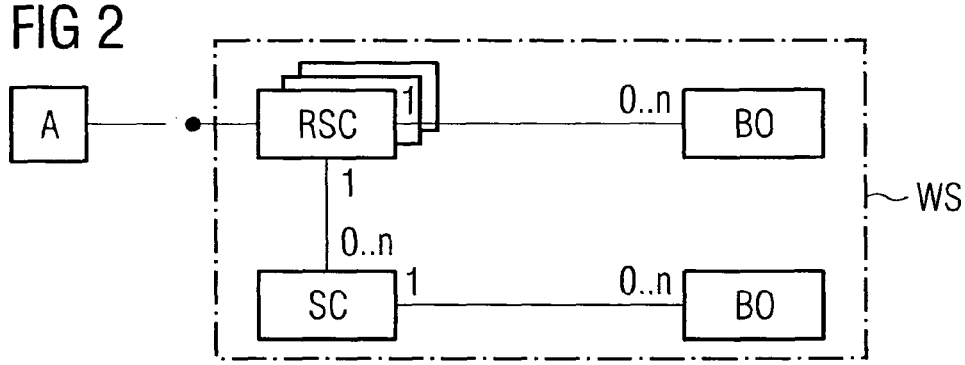
FIG. 2 A basic configuration of a web service according to an example embodiment of the invention.

FIG. 2 shows the numbers "1" and "0 ... n" along the connecting lines between the individual components of a web service WS, meaning between the remote service component RSC and the business object BO and to the service component SC, as well as between the service component SC and the business object BO. These numbers are intended to show, for example, that a remote service component RSC can offer no or several business objects BO. In addition, a remote service component RSC can also use no or several service components SC. In the same way, a service component SC respectively can comprise no or several business objects BO.

One important feature of an embodiment of the present application is that a specific set of medical web services WS is made available, wherein these are combined into a set that is specifically directed toward the medical domain. With these seven web services WS it is possible to cover and/or provide and make available all functionalities for medical applications A.

The example embodiment of the web services WS comprises seven web services:
 a transfer management service T;
 a data management service D;
 a workflow management service W;
 a report management service R;
 a protocol management service P'
 an operating management service O;
 an enterprise application integration management service E.

However, it is possible at any time to change this number with the aid of other advantageous embodiments. For less complex embodiments, only some of the previously mentioned services can be provided. In the same way, it is possible to replace the aforementioned services with other services or to expand the list with additional web services WS.

The individual web services WS are explained in the following in connection with FIGS. 3 to 9.

Figure 3:
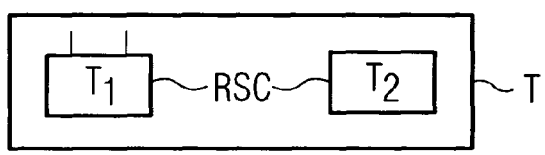
FIG. 3 A schematic representation of the basic configuration of a transfer management service.

FIG. 3 shows the transfer management T, which comprises two remove service components RSC: a media access component T1 and a network listener component T2.

Figure 4:
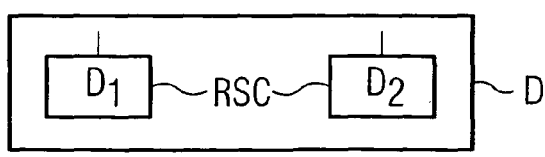
FIG. 4 A schematic representation of the basic configuration of a data management service.

The data management service D also comprises two remote service components RSC: a data management component D1 and a file access component D2, as shown in FIG. 4.

Figure 5:
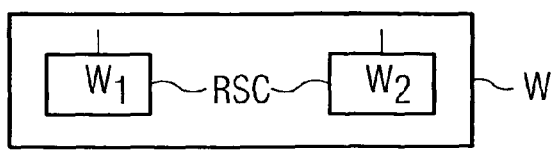
FIG. 5 A schematic representation of the basic configuration of a workflow management service.

The workflow management service W also comprises two remote service components RSC, as shown in FIG. 5, which include a workflow component W1 and an information component W2.

Figure 6:
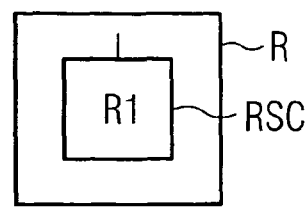
FIG. 6 A schematic representation of the basic configuration of a report management service.

The report management service R for one example embodiment comprises only one remote service component RSC: namely the common reporting data component R1, as shown in FIG. 6.

Figure 7:
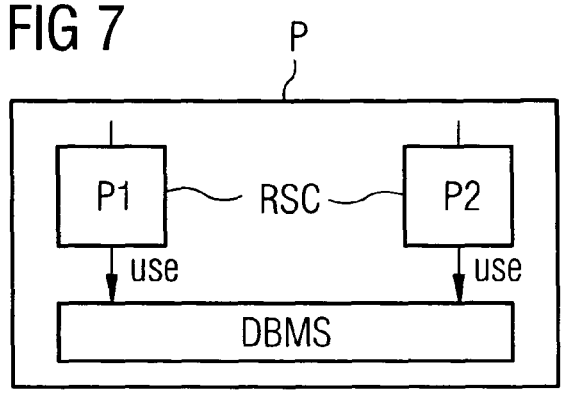
FIG. 7 A schematic representation of the basic configuration of a protocol management service.

FIG. 7 shows that the protocol management service P comprises two remote service components RSC, namely a protocol management component P1 and a protocol distribution component P2, which can both make use of a database management system DBMS.

Figure 8:
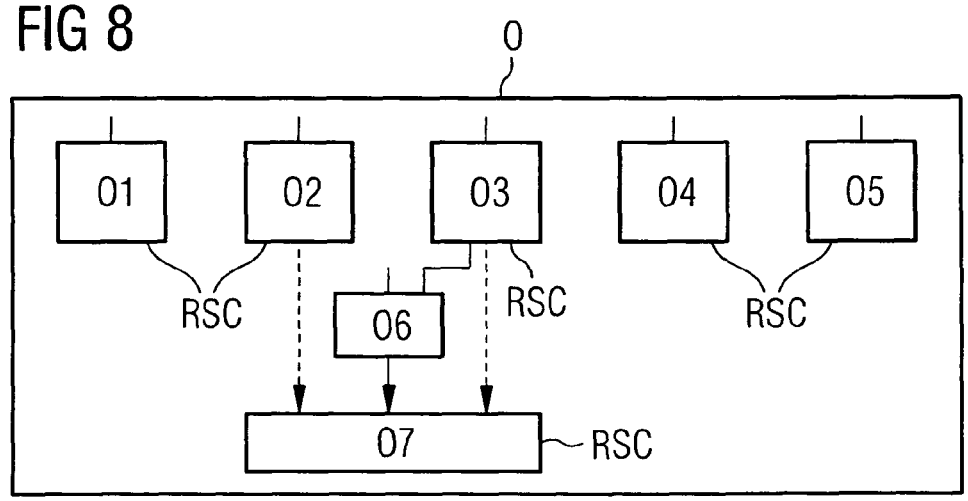
FIG. 8 A schematic representation of the basic configuration of an operating management service.

The operating management service O shown in FIG. 8 comprises seven remote service components RSC: a GSM component 05, a CoLicense component 04, a message-store component 07, a central-audit component 06, a central-utilization component 03, a central log component 02 and a depot component 01.

Figure 9:
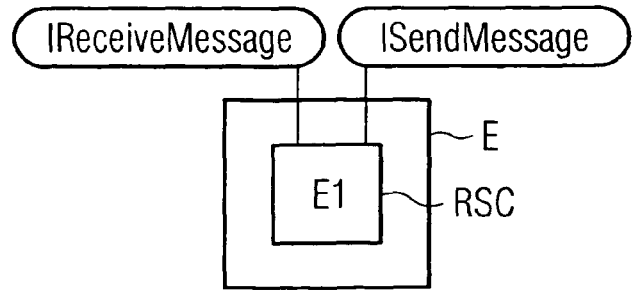
FIG. 9 A schematic representation of the basic configuration of an enterprise application integration management service.

The enterprise application integration management service E is shown in FIG. 9 and comprises only one remote service component RSC, namely a so-called OpenLink component E1. The OpenLink component E1 implements the OpenLink protocol and preferably offers only two interfaces to external services, IReceiveMessage and ISendMessage, as indicated in FIG. 9.

For example, a medical viewing application could access the data management service D, the enterprise application integration management E, the transfer management T and the technical architecture component (not described further herein) for displaying CT, MR and/or US images on a monitor or for browsing. The application A uses the data management D for loading and storing images and for indexing these, so that they can be found quicker later on.

The application A furthermore uses the transfer management service T for transmitting images from other computer-supported nodes in a network and/or to send them to other nodes.

Finally, the application A uses the enterprise application integration management service E for communicating via the HL7 standard protocol with a hospital information system (e.g. a RIS or radiology information system or a HIS, meaning a hospital information system).

An important feature of an embodiment of the present invention is that all web services WS that are used can be addressed via a uniform interface. The services are preferably addressed by the application A in a programming language-independent, platform-independent description language. The WSDL (web service description language) in particular is used as the description language for the network services WS for exchanging messages based on XML.

The above example was directed toward an application A, designed for displaying medical images with different modalities and/or to display them on a monitor.

A further example is a browsing application A, which will be explained further in the following. The browsing application A uses five web services WS: the workflow management W, a technical architecture component, the data management D, an application infrastructure component web service and the transfer management service T.

The browsing application A uses the workflow management W to start specific applications A if a user clicks on the indicated image.

The application A furthermore uses the data management D to obtain a list of the available images, which list is then shown to the user.

Finally, the application A uses the transfer management service T to obtain a list of images, which are not available locally. Once the images are obtained, this list is also shown to the user.

According to one example embodiment, the transfer management service T is designed for the transfer of medical DICOM image data. It contains functionalities for transferring image data in the DICOM format between two different data systems. One advantageous expansion of the transfer management service T can be to provide data transfer service outside of the network, for example to access data from other medical devices and vice versa to make available data from other external instances.

The data management service D makes available basic functionalities for storing and indexing and/or referencing medical DICOM image data, so that these can be detected quickly during a search. It comprises in particular hardware-type functions for reading, writing and deleting data and/or files, especially local or external hard drives, internal or external data storage devices, portable data carriers such as USB sticks or the like. According to one advantageous modification, the data management service D additionally comprises access rules and relates to the distribution and administration of user-specific access and use rights for individual data sets.

The report management service R provides basic functionalities for the manual, semi-automatic or automatic preparation of medical reports. According to one advantageous modification, the report management service R can additionally comprise functionalities for automatically reading medical reports. Text components for a uniform reporting can furthermore be provided for the purpose of automatically preparing reports.

One advantage of the solution according to an embodiment of the invention is that the different web services WS are basically completely independent of each other and can be configured based on the same or different configuration principles, wherein different versions of the web services WS can advantageously also be combined.

In conclusion, we want to point out that the description of the invention and the example embodiments should not be understood as restricting in view of a specific physical realization of the invention. It is especially obvious to one skilled in the art that the invention can be realized in part or completely with the aid of software and/or hardware and/or several physical products, in particular also computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

REFERENCE LIST

A application
BO business object
D data management
D1 data management component
D2 file access component
E enterprise application integration management
E1 OpenLink interface
F framework
O operating management
O1 depot component
O2 central-log component
O3 central-utilization component
O4 CoLicenseManager component
O5 GSM component
O6 central-audit component
O7 message-store component
P protocol management
R report management
R1 reporting-data component
RSC remote-service component
SC service component
T transfer management
T1 media-access component
T2 network-listener component
W workflow management
W1 workflow component
W2 information component
WS web service

What is claimed is:

1. A computer-implemented system for providing a number of web services for at least one medical application in the field of image-processing medical technology, so as to make available all-encompassing basic functionalities to the medical applications, the system comprising:
a processor; and
a memory, wherein one web service is configured to implement at least one basic functionality, all web services are respectively configured substantially identically, and all web services include:
at least one remote service component, to allow respectively one application to access at least one web service;
at least one business object component, in which the respective basic functionality is implemented, useable by a remote service component; and
at least one service component, which makes available different basic functionalities and which is useable by a remote service component,
wherein the basic functionalities are selectable from a number of functionalities including transfer management, data management, workflow management, report management, protocol management, operating management and enterprise application integration management.

2. The system according to claim 1, wherein the application is a medical viewing application and the basic functionality made available by the web service covers all functionalities of the viewing application.

3. The system according to claim 1, wherein the web service is accessible by the application, directly or indirectly via a framework.

4. The system according to claim 1, wherein the web services are realizable in at least one of a development environment for the one application and a runtime environment for the one application.

5. The system according to claim 1, wherein the web services provided to the application are addressed in a programming language-independent and platform-independent description language.

6. The system according to claim 5, wherein the programming language-independent and platform-independent description language is WSDL.

7. The system according to claim 1, wherein the system is based on a programming language-independent, platform-independent and protocol-independent architecture.

8. The system according to claim 1, wherein
at least two remote service components are provided,
the at least two remote service components are configured uniformly, and
the at least two remote service components are based on a same configuration diagram.

9. The system according to claim 8, wherein the remote service components are further configured for different web services.

10. The system according to claim 1, wherein a first web service is replaceable by a second web service without having to change the application, which uses the first or second web service.

11. The system according to claim 1, wherein the transfer management service implements basic functionalities for the transfer of DICOM image sets.

12. The system according to claim 1, wherein the transfer management service includes two remote service components including a media access component to provide information on available storage media on a computer and their characteristics, and a network-listener component to monitor a port on a machine for the data transfer and, if necessary, automatically initiate additional processing.

13. The system according to claim 1, wherein the data management service implements basic functionalities for accessing data.

14. The system according to claim 13, wherein the data management service implements basic functionalities for accessing DICOM image data sets.

15. The system according to claim 1, wherein the access to the data management service is at least one of a write and read access.

16. The system according to claim 1, wherein the data management service includes two remote service components including a data management component to implement access to an index repository for DICOM data, and a file access component to implement access to a file system of a computer that is not integrated into a network.

17. The system according to claim 1, wherein the workflow management service is configured to control an interaction between different medical applications.

18. The system according to claim 1, wherein the workflow management service includes two remote service components including a workflow component to generate clinical procedures within a framework of work lists, to coordinate the clinical procedures with respective required applications, to automatically start the required applications, and to create a link between data and applications, and an information component to administer at least one of patient data and performed procedure steps.

19. The system according to claim 1, wherein the report management service implements the basic functionality for combining application-specific partial reports into a uniform medical report.

20. The system according to claim 1, wherein the report management service includes a remote service component including a common reporting data component to transfer individual partial reports to a joint data model and to consolidate the data to prepare one report.

21. The system according to claim 1, wherein the protocol management service implements the basic functionality for administering and distributing protocols within a framework of image data acquisition.

22. The system according to claim 1, wherein the protocol management service includes two remote service components including a protocol management component to provide access to a database for the acquisition protocols so as to administer these, and a protocol distribution component to implement the distribution of the protocols and, in the process, communicate with several medical devices.

23. The system according to claim 1, wherein the operating management service includes several all-encompassing basic functionalities and implements a monitoring of system resources and system operation.

24. The system according to claim 1, wherein the operating management service includes seven remote service components including a GSM component, a CoLicense manager component, a message store component, a central audit component, a central utilization component, a central log component and depot component.

25. The system according to claim 1, wherein the enterprise application integration management service implements basic functionalities for communicating with other medical systems via the exchange of messages.

26. The system according to claim 1, wherein the enterprise application integration management service implements basic functionalities for at least one of sending and receiving messages.

27. The system of claim 1, wherein the web service is configured to expose application programming interfaces (APIs), the APIs including interfaces of the at least one remote service component.

28. A computer implemented method for providing a number of basic functionalities that encompass all applications at least for a medical application in the field of the image-processing medical technology, wherein respectively one web service implements at least one basic functionality and wherein all web services respectively have substantially the same basic configuration, the method comprising:
 providing at least one web service, wherein the web service includes,
  at least one remote service component;
  at least one business object in which the respective basic functionality is implemented and which is useable by a remote service component, and
  at least one service component that provides selected, different basic functionalities and is useable by a remote service component; and
 providing access for the application to at least one web service via at least one remote service component, wherein the basic functionalities are selectable from a number of functionalities including transfer management, data management, workflow management, report management, protocol management, operating management and enterprise application integration management.

29. A non-transitory computer readable medium, loadable into a computer memory, with commands readable by the computer for implementing the method as disclosed in claim 25 when the commands are realized on the computer.

30. The method of claim 28, wherein the at least one web service is configured to expose application programming interfaces (APIs), the APIs including interfaces of the at least one remote service component.

* * * * *